US007069790B1

(12) United States Patent
Dwyer

(10) Patent No.: US 7,069,790 B1
(45) Date of Patent: Jul. 4, 2006

(54) SYSTEMS AND METHODS FOR MEASURING RELATIVE THERMAL EXPANSION COEFFICIENT OF LOW THERMAL COEFFICIENT OF EXPANSION MATERIALS

(75) Inventor: Paul W. Dwyer, Seattle, WA (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/908,571

(22) Filed: May 17, 2005

(51) Int. Cl.
*G01B 7/16* (2006.01)
(52) U.S. Cl. ...................................................... 73/778
(58) Field of Classification Search .................. 73/778
See application file for complete search history.

(56) References Cited

U.S. PATENT DOCUMENTS

| 4,498,344 | A | * | 2/1985 | Dinger | 73/778 |
| 5,005,413 | A | * | 4/1991 | Novack et al. | 73/514.29 |
| 5,501,103 | A | * | 3/1996 | Woodruff et al. | 73/514.29 |
| 6,145,380 | A | * | 11/2000 | MacGugan | 73/493 |
| 6,207,470 | B1 | * | 3/2001 | De Bortoli | 438/53 |
| 6,230,565 | B1 | * | 5/2001 | Foote | 73/514.29 |
| 6,282,959 | B1 | * | 9/2001 | Blake et al. | 73/504.16 |
| 6,435,029 | B1 | * | 8/2002 | Hulsing et al. | 73/514.29 |
| 6,634,231 | B1 | * | 10/2003 | Malametz | 73/514.01 |
| 6,789,053 | B1 | * | 9/2004 | Collins | 703/2 |
| 6,938,334 | B1 | * | 9/2005 | Yu | 29/830 |

* cited by examiner

*Primary Examiner*—Max Noori
(74) *Attorney, Agent, or Firm*—Black Lowe & Graham PLLC

(57) ABSTRACT

Systems and methods for accurately comparing the thermal expansion coefficient of components (materials substrate, etc.) to be attached in some manner. This invention utilizes the frequency output of a double-ended quartz resonator bonded to first and second reference components to generate waveforms when the components are subjected to a temperature change. The waveforms are compared to determine the thermal expansion compatibility of the components.

12 Claims, 3 Drawing Sheets

SYSTEMS AND METHODS FOR MEASURING RELATIVE THERMAL EXPANSION COEFFICIENT OF LOW THERMAL COEFFICIENT OF EXPANSION MATERIALS

BACKGROUND OF THE INVENTION

Performance of precision instrumentation, such as accelerometers, may be affected by differences in the thermal coefficient of expansion of components that are in intimate contact with one another. As the temperature changes, stresses build up between the components, which may be difficult to model, especially if the stress buildup leads to slippage at the interface.

Therefore, there exists a need for systems and methods to measure the relative thermal expansion coefficient of components that are to be bonded together or attached by some means.

BRIEF SUMMARY OF THE INVENTION

The present invention provides systems and methods for accurately comparing the thermal expansion coefficient of components (materials substrate, etc.) to be attached in some manner. The embodiments of the present invention utilize the frequency output of a first double-ended quartz resonator bonded to a first reference component and a second double-ended quartz resonator bonded to a second reference component to generate waveforms when the components are subjected to a temperature change. The waveforms are compared to determine the thermal expansion compatibility of the components.

BRIEF DESCRIPTION OF THE SEVERAL VIEWS OF THE DRAWING

The preferred and alternative embodiments of the present invention are described in detail below with reference to the following drawings.

DETAILED DESCRIPTION OF THE INVENTION

Figure 1:
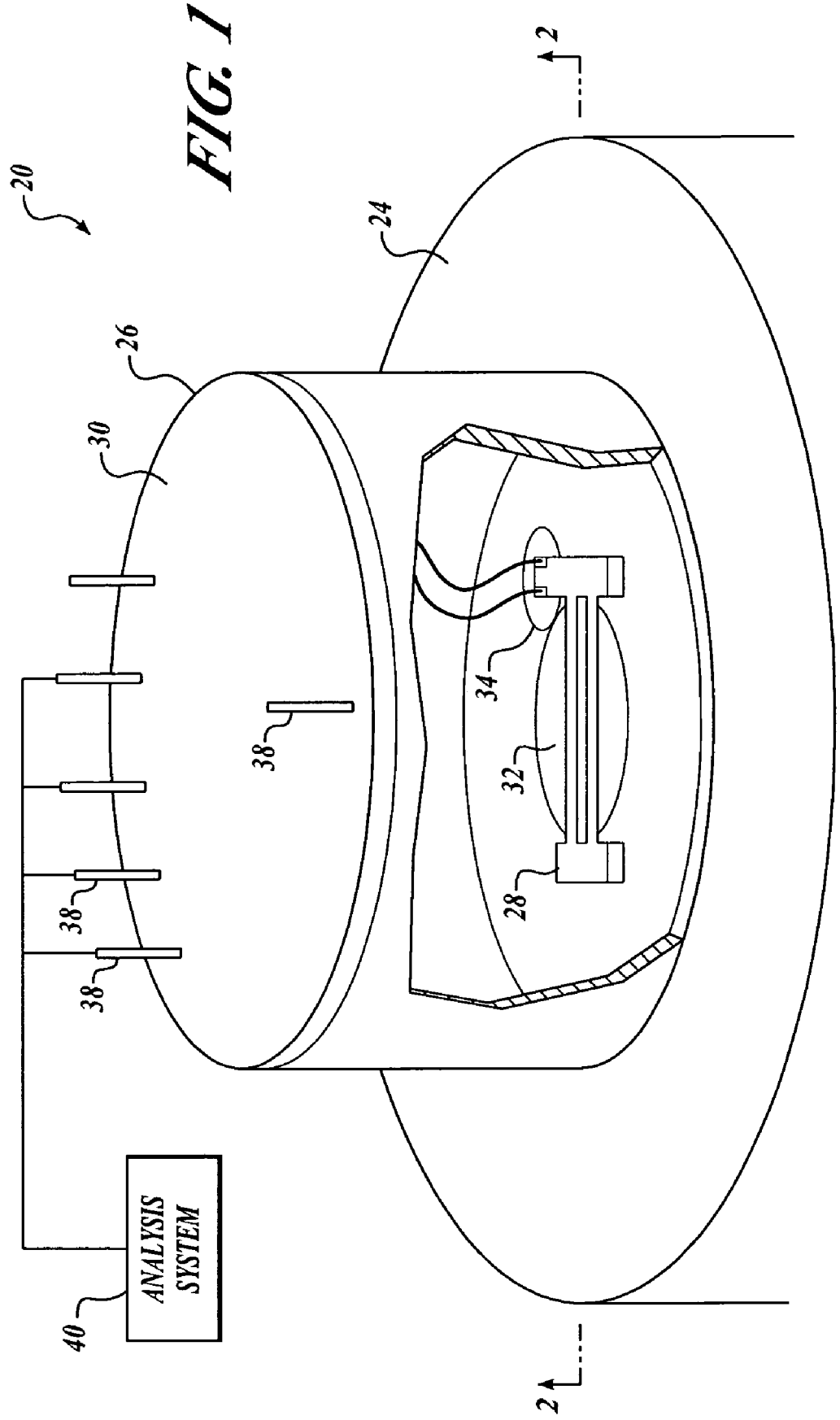
FIG. 1 illustrates a perspective view of an embodiment of the present invention.
Figure 2:
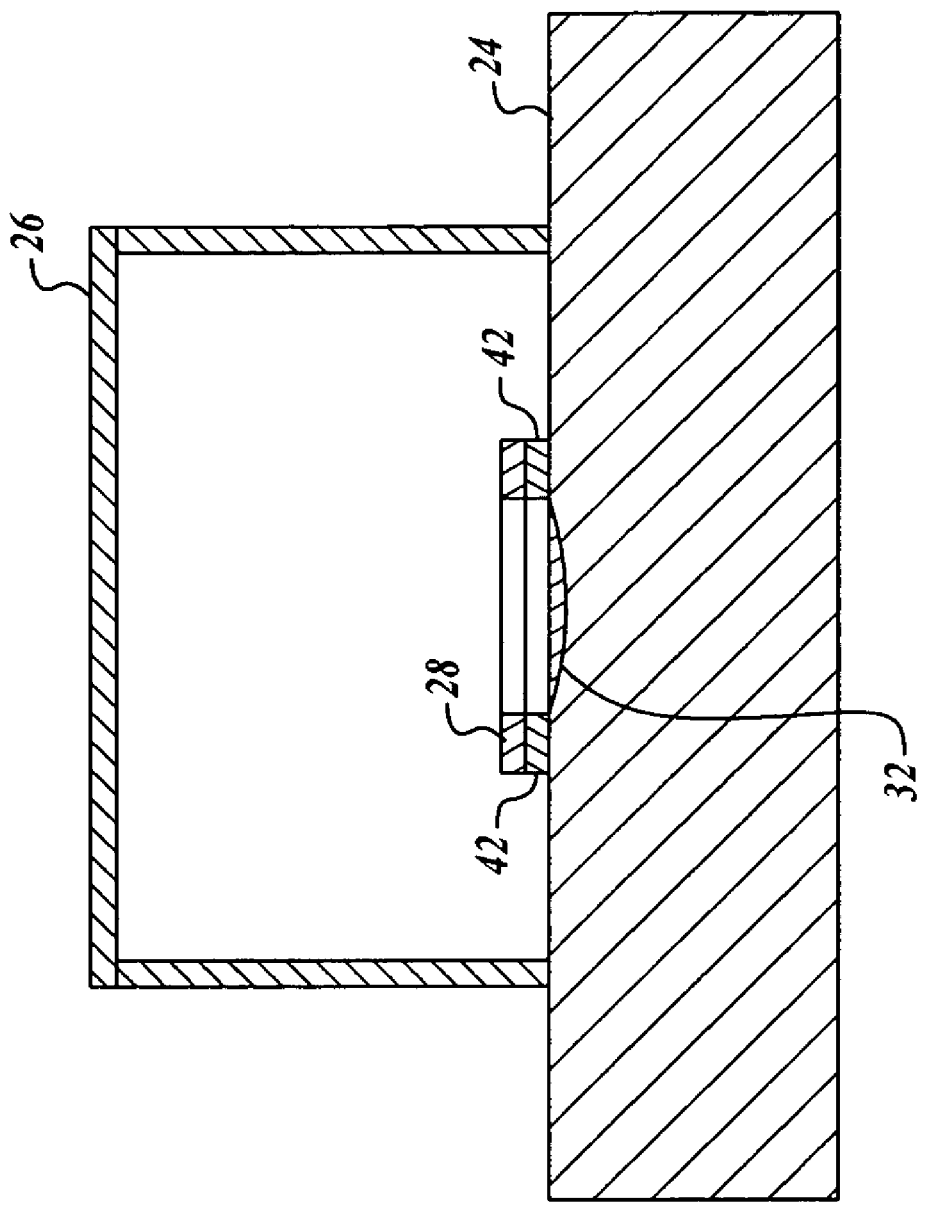
FIG. 2 illustrates a cross-sectional view of the present invention shown in FIG. 1.

FIGS. 1 and 2 illustrate an example application of a system 20 for measuring thermal expansion coefficient of a reference material 24. In one embodiment, the system 20 includes a hybrid resonator device 26. The hybrid resonator device 26 includes a resonating device 28 (e.g., double-ended tuning fork, or other resonating crystal) and a hybrid resonator circuit 30 with housing. Electrical leads connect the resonator device 28 to the hybrid resonator circuit 30 within the housing.

In this example, the resonating device 28 is a double-ended tuning fork (DETF). Ends of the DETF are mounted on the reference material 24. The ends of the DETF may be attached to the reference material 24 in a number of ways, for example, non-conductive mounting pads may reside between the reference material 24 and the corresponding ends of the DETF. The mounting pads may be attached to the substrate using a non-filled epoxy resin, such as Ablebond 931-1 by Ablestick Laboratories. Other materials may be used for this application, however the required cure temperature is a consideration along with the thermal expansion coefficient mismatch of the resonator device 26 to the substrate (reference material 24) for survivability of the resonator device 26. For example, if the expansion coefficient of the reference material 24 matched that of the resonator device 26, the parts could be brazed together to reduce hysteresis effects of the epoxy. For many applications, this is not an issue since these effects will common-mode out.

In one embodiment, the reference material 24 is machined in order to provide reliefs 32 and 34. The relief 32 is positioned such that tines of the DETF are free to vibrate without electrically and/or physically contacting the reference material 24. The relief 34 is positioned under the contacts and between the electrical leads and the corresponding end of the DETF. The relief 34 reduces any parasitic capacitance between the surface of the reference material 24 and the electrical leads and the corresponding end of the DETF. The reliefs 32 and 34 may be produced by any number of different methods, such as by ultrasonic machining in the case where the reference material 24 is a quartz substrate. Alternative methods of producing the required relief zones in the substrate include wet chemical etching for many dielectric materials, DRIE (deep reactive ion etching) for silicon or conventional milling for metals.

The hybrid resonator circuit 30 receives the electrical leads. In one embodiment, the circuit 30 makes up a top section of the housing. The circuit 30 includes one or more output pins 38. The hybrid resonator circuit 30 outputs a signal (e.g., digital) through one or more of the pins 38 based on the vibrating frequency of the DETF.

Once the hybrid resonator device 26 has been attached to the reference material 24, testing begins. The housing may be attached to the reference material with a silicone elastomer, such as DC96-083 or other suitable elastomeric materials which will not transmit stress to the substrate. Further, the support structure for the hybrid can be made sufficiently flexible so as not to affect the geometry changes over temperature of the substrate. Testing includes subjecting the system 20 to a heating and/or cooling process based upon the type of reference material used. The frequency output of the resonating device 28 is measured and is output by the hybrid resonator circuit 30, and sent to an analysis system 40. The sinusoidal signal from the resonating device 28 is fed into an open-loop amplifier that produces a 5 volt square wave.

Figure 3:
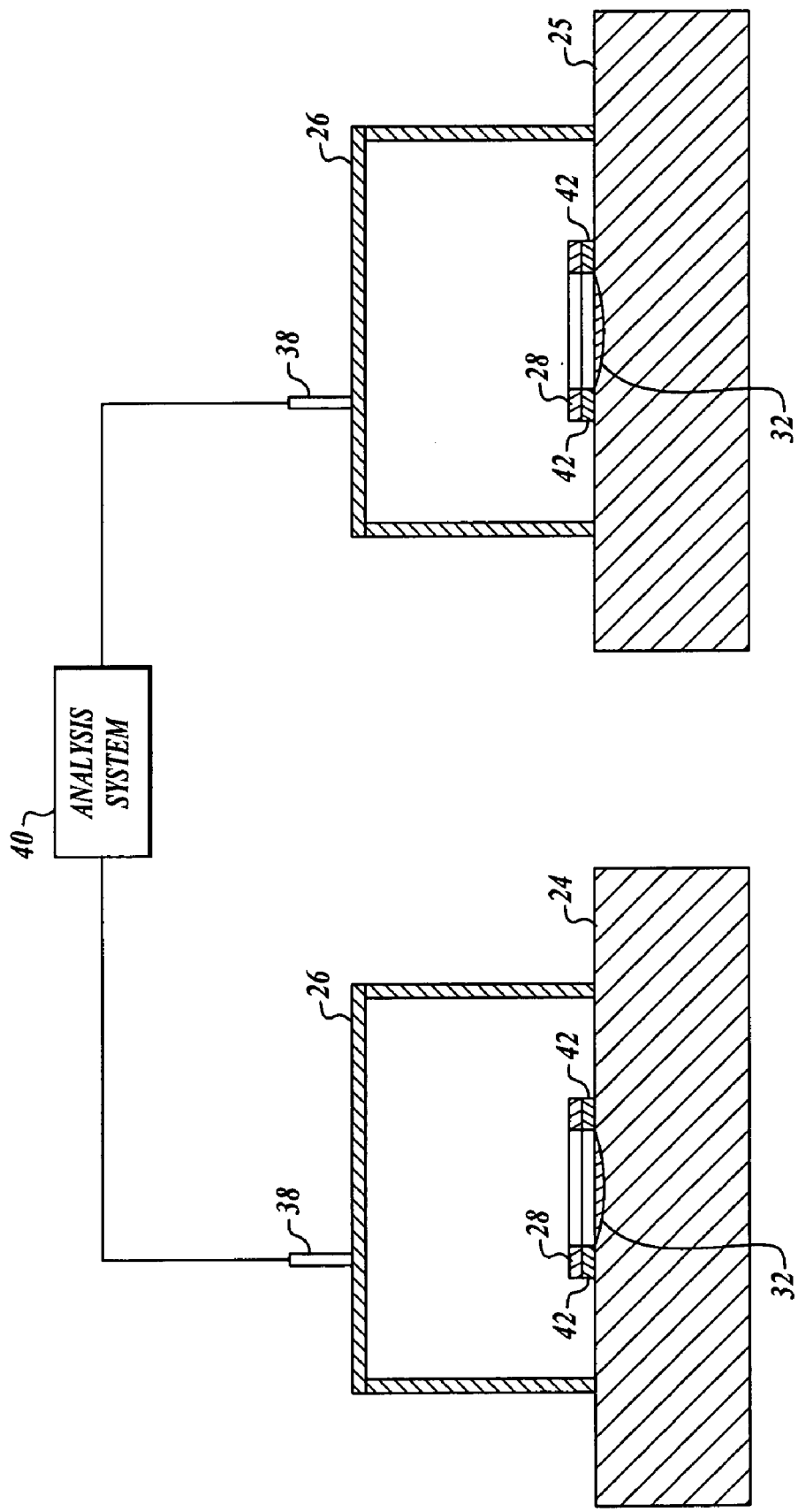
FIG. 3 illustrates a cross-sectional view of an embodiment of the invention as it applies to two reference materials.

FIG. 3 illustrates that the analysis system 40 also receives a frequency waveform from another resonator system identical to the first resonator system that is testing a second reference material 25 that is to be bonded to the presently tested material 24. The analysis system 40 tracks the temperature and subtracts the waveform of the second material 25 from the waveform produced in association with the reference material 24 to produce a difference value. The difference value is integrated over temperature in order to indicate the level of stress that builds up between the two disparate materials. The range for the integration is over the temperature span of interest and is limited only by the applied stress the resonator can take and the ability of the electronics to survive (~200 C.). In one embodiment, the reference material (substrate) is prepared such that a clearance trench is produced to avoid interference with the resonating beam of the resonator. A second trench is included to avoid excessive capacitance between metallization traces on the resonator and the substrate. The resonator, which has wire bonds attached in advance, is then bonded to the substrate. A circuit coupled to the wire bonds resonates the double-ended tuning fork and measures its frequency. The reference material with attached resonator and circuit is placed in an oven or cooler and heated or cooled to the desired temperatures. When in the oven or cooler the frequency of the resonator is measured and captured for analysis. The waveform produced during the heating or cooling process is then subtracted from the waveforms of other materials undergoing the same thermal test. Integrating the difference indicates the level of stress built up between the materials. This is particularly useful when one material is an alloy whose thermal expansion coefficient can be adjusted by small modifications of element ratios.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

What is claimed is:

1. A method comprising:
   attaching a double-ended tuning fork to a first reference material;
   attaching a second double-ended tuning fork to a second reference material;
   applying a pre-defined thermal test scenario to the first and second materials;
   recording output of the first and second double-ended tuning forks produced during the thermal test scenario; and
   determining a relative stress value between the first and second materials based on the recorded outputs of the first and second double-ended tuning forks.

2. The method of claim 1, wherein determining includes subtracting the output of the first double-ended tuning fork from the output of the second double-ended tuning fork, and integrating the result of the subtraction.

3. The method of claim 1, further comprising:
   machining one or more trenches in the first and second materials prior to attaching of the double-ended tuning forks.

4. The method of claim 1, wherein the double-ended tuning forks are similar in size and construction materials.

5. The method of claim 1, further comprising:
   applying a driving signal to the first and second double-ended tuning forks during the application of the pre-defined thermal test scenario.

6. An apparatus for comparing reference materials, the apparatus comprising:
   a first double-ended tuning fork attached to a first reference material for outputting a first vibration signal produced during a thermal test scenario;
   a second double-ended tuning fork attached to a second reference material for outputting a second vibration signal produced during the thermal test scenario; and
   a component configured to determine a relative stress value between the first and second reference materials based on the first and second vibration signals.

7. The apparatus of claim 6, wherein component subtracts the first vibration signal from the output of the second vibration signal and integrates the result of the subtraction.

8. The apparatus of claim 6, wherein the first and second reference materials include one or more trenches.

9. The apparatus of claim 6, wherein the double-ended tuning forks are similar in size and construction materials.

10. The apparatus of claim 6, further comprising:
    a second component configured to apply a driving signal to the first and second double-ended tuning forks during the pre-defined thermal test scenario.

11. An apparatus for comparing reference materials, the apparatus comprising:
    a first resonator attached to a first reference material for outputting a first vibration signal produced during a thermal test scenario;
    a second resonator attached to a second reference material for outputting a second vibration signal produced during the thermal test scenario; and
    a component configured to determine a relative stress value between the first and second reference materials based on the first and second vibration signals.

12. The apparatus of claim 11, wherein the resonators are similar double-ended tuning forks.

* * * * *